(12) United States Patent
Goebel et al.

(10) Patent No.: US 8,987,681 B2
(45) Date of Patent: Mar. 24, 2015

(54) IONIZATION METHOD, ION PRODUCING DEVICE AND USES OF THE SAME IN ION MOBILITY SPECTROMETRY

(75) Inventors: Johann Goebel, Munich (DE); Andreas Langmeier, Munich (DE); Matthias Kessler, Munich (DE)

(73) Assignee: EADS Deutschland GmbH, Ottobrunn (DE)

( * ) Notice: Subject to any disclaimer, the term of this patent is extended or adjusted under 35 U.S.C. 154(b) by 36 days.

(21) Appl. No.: 13/499,506

(22) PCT Filed: Aug. 26, 2010

(86) PCT No.: PCT/EP2010/062510
§ 371 (c)(1),
(2), (4) Date: Jun. 11, 2012

(87) PCT Pub. No.: WO2011/039010
PCT Pub. Date: Apr. 7, 2011

(65) Prior Publication Data
US 2012/0235032 A1 Sep. 20, 2012

(30) Foreign Application Priority Data

Sep. 30, 2009 (DE) .......................... 10 2009 043 739
Oct. 1, 2009 (DE) .......................... 10 2009 048 063

(51) Int. Cl.
*G01N 27/64* (2006.01)
*H01J 49/00* (2006.01)
*H01J 49/16* (2006.01)

(52) U.S. Cl.
CPC ............ *H01J 49/0027* (2013.01); *G01N 27/64* (2013.01); *H01J 49/0031* (2013.01); *H01J 49/162* (2013.01)

USPC ..... 250/423 P; 250/282; 250/288; 250/423 R (58) Field of Classification Search
CPC .... G01N 27/622; H01J 49/164; H01J 49/446; H01J 49/0059
USPC .............................. 250/288, 282, 287, 423 R
See application file for complete search history.

(56) References Cited

U.S. PATENT DOCUMENTS 4,707,602 A 11/1987 Knorr
5,719,392 A * 2/1998 Franzen ........................ 250/282
(Continued)

FOREIGN PATENT DOCUMENTS

DE 102 47 272 A1 4/2004
DE 103 06 900 A1 9/2004
(Continued)

OTHER PUBLICATIONS

Corresponding International Search Report with English Translation dated Mar. 28, 2011 (six (6) pages).
(Continued)

*Primary Examiner* — Jack Berman
*Assistant Examiner* — Kevin Chung
(74) *Attorney, Agent, or Firm* — Crowell & Moring LLP (57) ABSTRACT

A method for ionizing, using pulses of ionization radiation, an analyte to be examined by way of ion mobility spectrometry using a pulse sequence is modulated with a known time-variable impression pattern is provided. An ionization device for carrying out the method and an ion mobility spectrometry method and an ion mobility spectrometry device that use the ionization method and/or the ionization device are also provided.

14 Claims, 7 Drawing Sheets

(56) References Cited

U.S. PATENT DOCUMENTS

| | | | |
|---|---|---|---|
| 6,049,076 | A | 4/2000 | Goebel et al. |
| 6,300,626 | B1 | 10/2001 | Brock et al. |
| 6,479,815 | B1 | 11/2002 | Goebel et al. |
| 2003/0146392 | A1* | 8/2003 | Kimmel et al. ............ 250/396 R |
| 2005/0230615 | A1* | 10/2005 | Furutani et al. ................ 250/287 |
| 2005/0253063 | A1* | 11/2005 | Tan et al. ...................... 250/288 |
| 2007/0075240 | A1* | 4/2007 | Hieke ............................ 250/282 |
| 2007/0080290 | A1 | 4/2007 | Parker et al. |
| 2007/0158543 | A1* | 7/2007 | Clowers et al. ................ 250/282 |
| 2007/0158545 | A1* | 7/2007 | Verentchikov ................ 250/282 |
| 2008/0173807 | A1* | 7/2008 | Yoon et al. .................... 250/282 |
| 2008/0185513 | A1* | 8/2008 | Belov et al. ................... 250/288 |
| 2008/0218102 | A1* | 9/2008 | Sliski et al. ................... 315/502 |
| 2009/0236514 | A1* | 9/2009 | Renner .......................... 250/282 |
| 2011/0031393 | A1* | 2/2011 | Goebel et al. ................. 250/286 |

FOREIGN PATENT DOCUMENTS

| | | |
|---|---|---|
| DE | 198 15 436 B4 | 4/2006 |
| DE | 198 61 106 B4 | 1/2008 |
| DE | 10 2007 057 3 | 5/2009 |
| EP | 0 848 253 B1 | 11/2001 |
| WO | WO 01/51917 A2 | 7/2001 |

OTHER PUBLICATIONS

Brian H. Clowers et al., "Hadamard Transform Ion Mobility Spectrometry", Anal Chem., 2006, pp. 44-51, vol. 78, No. 1, American Chemical Society.

F.J. Knorr et al., "Fourier Transform Ion Mobility Spectrometry", Anal Chem., 1985, pp. 402-406, vol. 57, No. 2, American Chemical Society.

Fritz J. Knorr et al., "Fourier Transform Time-of-Flight Mass Spectrometry", Analytical Chemistry, 1986, pp. 690-694, vol. 58, No. 4, American Chemical Society.

M. Misakian et al., "Drift tubes for Characterizing Atmospheric Ion Mobility Spectra using ac, acPulse, and Pulse Time-of-Flight Measurement Techniques", Rev. Sci. Instrum. 1989, pp. 720-729, vol. 60, No. 4.

Ruth A. Dyer et al., "Right-Cyclic Hadamard Coding Schemes and Fast Fourier Transforms for Use in Computing Spectrum Estimates and Hadamard-Transform Spectrometry", IEEE Transactions on Instrumentation and Measurement, 1996, pp. 860-864, vol. 45, No. 5.

* cited by examiner

IONIZATION METHOD, ION PRODUCING DEVICE AND USES OF THE SAME IN ION MOBILITY SPECTROMETRY

BACKGROUND AND SUMMARY OF THE INVENTION

Exemplary embodiments of the invention relate to an ionization method for an analyte to be examined using ion mobility spectrometry. The invention also relates to an ion mobility spectrometry method for determining an analyte by means of ion mobility spectrometry using such an ionization method. The invention furthermore relates to an ion producing device for an ion mobility spectrometer. Finally, the invention relates to an ion mobility spectrometer using such an ion producing device.

The invention lies in the field of ion mobility spectrometry, which, in recent times, has found ever increasing use in the detection of very small traces of analytes. In particular, ion mobility spectrometry (also abbreviated to IMS below) is used to detect illicit drugs, explosive materials and chemical warfare agents. According to the basic principle, a generally gaseous sample material is subjected to an ionization method, whereupon the individual ionized components of the sample mixture are separated by virtue of the fact that they are accelerated by an electric field and a substance-specific or molecule-specific time-of-flight is measured over a specific measuring distance in a drift gas—possibly in the counter-flow of the drift gas.

The drift distance acting as measuring distance is generally situated within a drift tube, at the beginning of which a gate electrode (also referred to as ion gate) is arranged. An ion collector is situated at the other end of the drift distance.

In conventional ion mobility spectrometers, the gate electrode at the beginning of the drift distance is opened for a brief period of time such that a sample of different ion species can drift to the ion collector. The duration of the opening time must be judiciously selected, optimized between contradictory prescriptions. Firstly, it needs to be short in order to minimize the peak width of the resulting drift spectrum. On the other hand, it must be as long as possible to enable the greatest possible number of ions to enter the drift tube. A further problem is connected to the previous standard masking techniques. The ion gate must remain closed until the last ion species has reached the ion collector. According to Knorr et al. [1]—the citation is referred to in more detail below—this loses up to 99% of the analyte molecules, which are continuously desorbed from the analysis sample and transported through an ionization chamber by the sample gas flow.

In conventional ion mobility spectrometers, the ion gate is formed by an electrically conductive grid at the beginning of the drift distance. The prior art has already disclosed various approaches for minimizing the ion loss occurring in such conventional ion mobility spectrometers as a result of the short ion gate opening time. To this end, reference is made to the following references, which constitute part of this disclosure:

[1] F. J. Knorr et al. Fourier Transform Ion Mobility Spectrometry, Analytical Chemistry, vol. 57, no. 2, pp. 402-406, February 1985.

[2] F. J. Knorr, Fourier Transform Time-of-Flight Mass Spectrometry, Analytical Chemistry, vol. 58, no. 4, pp. 690-694, April 1986.

[3] M. Misakian et al., Drift tubes for characterizing atmospheric ion mobility spectra using ac, ac-pulse, and pulse time-of-flight measurement techniques, Rev. Sci. Instrum., vol. 60, no. 4, pp. 720-729, Apr. 198.

[4] B. K. Clowers, W. F. Siems, H. H. Hilland, S. M. Massick, Hadamard Transform Ion Mobility Spectrometry, Anal. Chem. 2006, 78, 44-51.

[5] R. A. Dyer and S. A. Dyer, Right-Cyclic Hadamard Coding Schemes and Fast Fourier Transforms for Use in Computing Spectrum Estimates in Hadamard-Transform Spectrometry.

References [1], [2] and U.S. Pat. No. 4,707,602 disclosed a method and a device for carrying out Fourier transform ion mobility spectrometry in which a specific pattern is impressed on the gate electrode, by means of which ions are passed through the gate electrode. In the process, a voltage at the gate electrode and the signal reaching the ion collector are simultaneously modulated by a periodic modulation function (gate function). By way of example, the modulation function could be a sine wave or a rectangular wave. A rectangular wave is used as a standard. The output gate is modulated at the same time by the same rectangular wave without a phase shift. This results in only ions that have a drift time of $1/v$, $2/v$ . . . etc. reach the collector, in which v denotes the frequency.

Then the frequency of the modulation function is modified e.g., continuously, while the relative shape thereof remains constant. The width of the frequency-change range determines the resolution of the transformed spectrum.

More precisely, the resolution of the drift-time spectrum inversely transformed from the interferogram is determined by:

(1) sampling frequency (2) Measured "Fourier frequencies". Ideally, all Fourier frequencies (Nyquist=Nyquist sampling frequency) should be measured. However, this is usually not possible. Particularly the low ones (e.g., O-frequency) are difficult.

(3) A sufficient number of periods must be measured for each frequency (this increases the measurement duration; a compromise may possibly need to be found here). This also co-determines the achieved resolution.

Then an output signal is produced as a function of the applied modulation frequency. This output signal is referred to as ion interferogram. The Fourier transform of this interferogram is subsequently calculated, from which the drift-time spectrum can be derived.

This allows the time to be encoded in a practical manner. The gate electrode and, simultaneously and with the same phase, the output electrode are held open with a specific frequency up to half of the time such that ions can pass therethrough. In the process, the ion current matching this frequency is established. The ions passing through at another frequency are characterized by this other frequency. A resolution of the corresponding run times is obtained if the recorded frequency spectrum is then transformed back into the time domain by a Fourier transform.

A similar method also works with other encoding methods. By way of example, it is also possible to modulate the gate electrode using a Hadamard code, as described in more detail in e.g. references [4] and [5]. Corresponding methods are referred to as Hadamard transform ion mobility spectrometry methods.

Further ion mobility spectrometers and the methods that can be carried out thereby are known from EP 0 848 253 B1, DE 198 61 106 B4, DE 10 2007 057 374 A1, DE 102 47 272 A1, and also from DE 198 15 436 B4 and DE 103 06 900 A1. In respect of more details of the different techniques in ion mobility spectrometry, reference is made to the aforementioned documents.

DE 103 06 900 A1, DE 102 47 272 A1 and DE 10 2007 057 374 A1 relate to ionization methods and ionization devices for use in ion mobility spectrometry for ionizing the analyte to be examined, the ionization being brought about by pulses from an ionizing radiation. To this end, this known ionization method uses a pulsed laser as ionization radiation source.

DE 103 06 900 A1 describes a spectrometer with laser arrangement for gas analysis in more detail. Here, the spectrometer comprises a chamber for holding a gas, an apparatus for producing a potential drop in the chamber, a laser-light source and an optical resonator, which is formed by opposing mirrors or configured as ring resonator. A laser beam for ionizing the gas is produced within the chamber. An ion collector serves for detecting the produced ions.

A similar device is described in DE 102 47 272 A1, with a multi-reflection cell being provided in place of an optical resonator made from opposing mirrors.

In the method as per DE 10 2007 057 374 A1, an absorption spectrometry method and a fluorescence measurement are also carried out in addition to such a laser ionization mobility spectrometry method using a laser ionization method.

A gate electrode can be dispensed with in the case of such laser ionization mobility spectrometry methods (also abbreviated to LIMS methods below). Individual laser pulses produce the ion species (directly or by subsequent chemical ionization). However, in all known LIMS methods, the laser pulse spacing must be at least as long as the drift time of the slowest ion species. This restricts the amount of analyte molecules.

In conventional ion mobility spectrometry, the timeframe between two ionization procedures is between 20 and 40 ms. These times are often too long, particularly if shorter measurement times are demanded, such as in e.g., a thermally induced desorption process, and a large part of the gas mixture available cannot be used for the measurement.

The previously known IMS equipment therefore has the disadvantages of a lower repetition rate and restricted detection sensitivity.

Exemplary embodiments of the present invention are directed to an ionization method and an ion producing device, by means of which higher sensitivity and greater measuring speed can be obtained in ion mobility spectrometers, which at the same time have a simple design.

According to a first aspect, the invention involves an ionization method for ionizing, using pulses of ionizing radiation, an analyte to be examined using ion mobility spectrometry, wherein a pulse sequence is modulated by a previously known time-variable impression pattern.

The modulation and demodulation becomes particularly simple if, as provided in an advantageous embodiment, the ionizing pulse sequence is modulated in a binary manner.

Particularly those patterns that have already been used in known gate voltage modulation methods in ion mobility spectrometry are suitable for advantageous impression patterns. Advantageously, use is made, in particular, of Hadamard encoding or Fourier-transform encoding.

Accordingly, in one embodiment of the invention, provision is made for a pulse sequence to be modulated at equidistant time intervals by an interval frequency, each interval constituting either an ON phase, during which at least one pulse is produced, or an OFF phase, during which no pulses are produced, with the sequence of ON phases and OFF phases being produced according to a previously known quasi-random pattern, more particularly a Hadamard pattern.

It is particularly preferred for a sequence of ON phases and OFF phases to be produced by a quasi-random pattern, more particularly by a Hadamard pattern.

According to one possible embodiment, a pulse sequence with a pulse frequency less than the interval frequency is produced within the ON phases. By way of example, the interval frequency can be an integer multiple of the pulse frequency. According to a more preferred embodiment, which was found to be particularly advantageous for precise measurements, precisely one pulse is produced in each ON phase. More preferably the pulse is respectively produced at the beginning of the ON phase.

In another advantageous embodiment, it is preferable for a sequence of intervals to be generated with an interval frequency, with, during the sequence of intervals, ON phases, during which at least one pulse or one pulse sequence is produced, and OFF phases, during which no pulses are produced, alternating with one another, with the interval frequency being modified to obtain a frequency spectrum.

It is particularly preferable for a pulsed laser to be used for producing the ionization pulses.

According to a preferred embodiment, pseudo-random patterns and any type of non-repetitive patterns can be used for the impression of very highly repetitive ionization patterns. Fourier encoding is also possible for a pattern for the impression. In this embodiment, which can also be referred to as LIMS-FT, signals are preferably measured in the frequency domain using periodically produced pulses and at least one correspondingly opening reception gate. The signals measured in the frequency domain are (inversely) transformed by FT (Fourier transform) into the drift-time domain. To this end, use can be made of an FFT (fast Fourier transform), i.e., an established computational method, which can easily be carried out by standard software, for calculating an FT.

In a preferred embodiment, a laser system is used for the ionization, which enables repetition rates of approximately 1 kHz up to the low MHz range.

Compared to conventional ion gate systems, the modulation according to the invention of the pulses of ionizing radiation with the impression pattern and, more particularly, the use of laser systems and other photon-based ionization methods offer the advantage of modulating an ion current with very high rates at the right time and without temporal restrictions.

By impressing a known time-variable pattern with a high repetition rate, it is possible to improve significantly the yield of an available analyte gas.

There is a virtually linear relationship between repetition rate and ion yield. As a result of using highly repetitive ionization pulse sources with a correspondingly impressed pattern, a substantially greater ion signal is obtained during the considered period of time than with any previously known ion mobility spectrometry method. Hence, this can advantageously ensure a higher detection sensitivity of the IMS method and/or use can be made of an ionization source (more particularly a laser), which need only provide a substantially lower output power. Particularly in the case of so-called laser IMS (LIMS), a lower output power contributes to a substantially better cost/benefit aspect at an improved power.

In particular, this allows the production of mobile IMS equipment, supplied by batteries or rechargeable batteries, with high detection sensitivity.

The methodology, presented here, according to the preferred embodiments of the invention provides a method in which ions, which originate from laser-induced two-photon ionization, can be used more efficiently than in standard LIMS configurations and can be used for a sensitive measurement of the mobility spectrum.

BRIEF DESCRIPTION OF THE DRAWING FIGURES

Exemplary embodiments of the invention are explained in more detail below on the basis of the attached drawings. In detail:

FIGS. 4, 4a, 4b show a schematic illustration of a third exemplary embodiment of a laser pulse sequence modulated by another impression pattern, in which, for illustration purposes, subfigure FIG. 4a shows an equidistant single-frequency clock function, with an autocorrelation function being illustrated in the subfigure FIG. 4b (FFT pattern);

DETAILED DESCRIPTION

Figure 1:
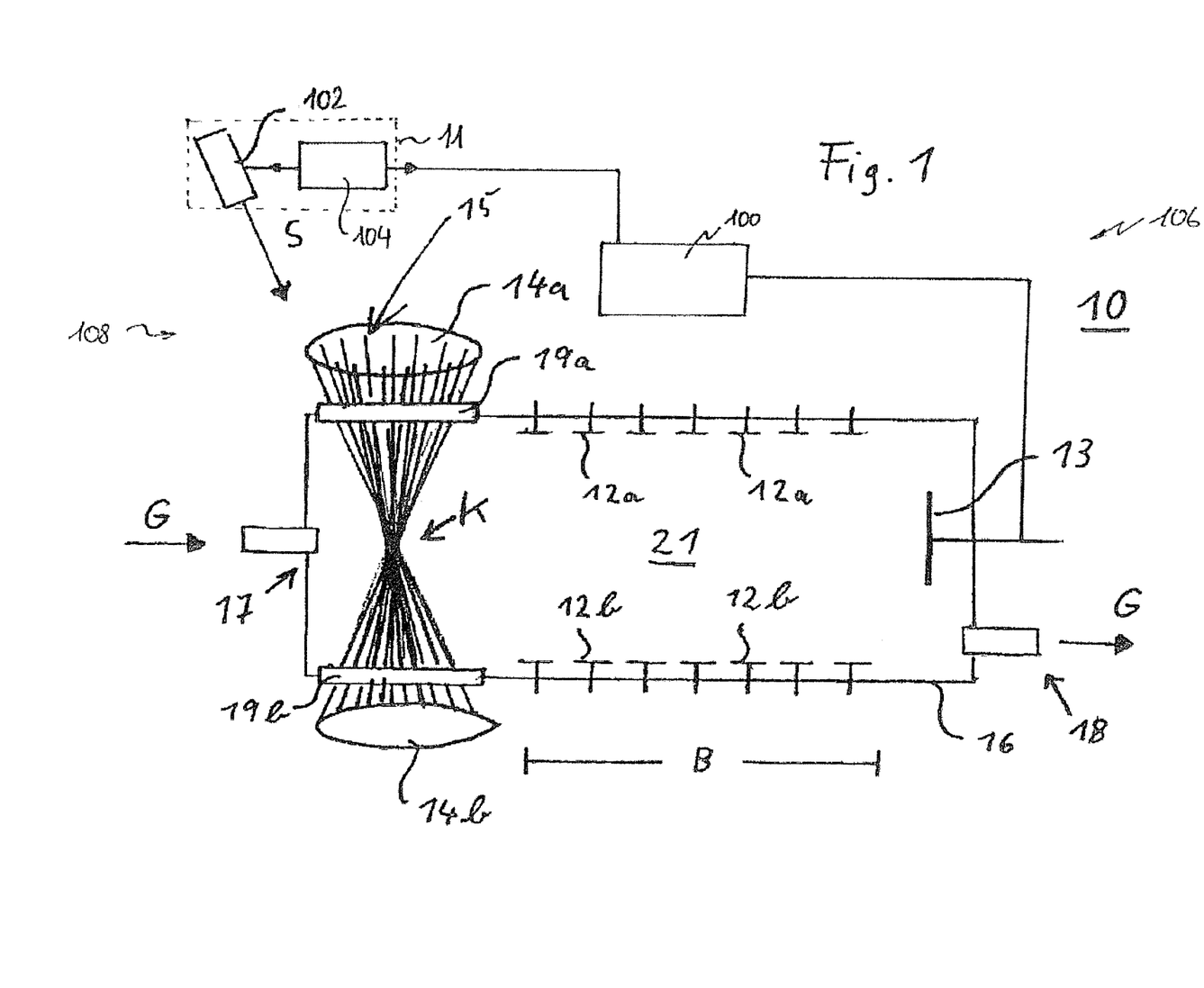
FIG. 1 shows a schematic, simplified illustration of an embodiment of a laser ion mobility spectrometer with an ion producing device, having a pulsed ionization radiation source and an encoding or modulating apparatus for encoding and/or modulating a pulse sequence from the ionization radiation source with a previously known time-variable impression pattern.

FIG. 1 shows a spectrometer 10 as a particularly preferred embodiment of the invention. Here, a laser 11 produces a laser beam S in the UV range so that during operation the laser beam interacts in the spectrometer 10 with a gas G to be analyzed in order to ionize substances (analytes) contained therein. An arrangement of a multiplicity of mutually opposing rows of electrodes 12a, 12b, together with a voltage source (not illustrated in the figure), forms an apparatus for producing a potential drop. As a result of the potential drop, ions entering the potential drop are accelerated. The corresponding entering ions pass through an acceleration distance B, which is formed by the opposing rows of electrodes 12a, 12b. An ion collector 13 serving to detect the produced ions is arranged at the end of the acceleration distance B. By way of example, the ion collector 13 is embodied as a separate electrode and electrically connected to a detection and/or analysis apparatus 100.

Two opposing mirrors 14a, 14b are arranged at the beginning of the acceleration distance B, or upstream thereof, in order to reflect the laser beam S to and fro a number of times between the mirrors 14a, 14b. Hence, the laser beam S entering through an opening passes over a multiplicity of path lengths between the mirrors 14a, 14b, and so the path of the laser beam S travelled in the gas is increased many times over and a more effective interaction between the laser beam S and the gas G is obtained thereby. Here, the mirrors 14a, 14b are optically configured such that respectively a multiplicity of reflection points 15 of the to-and-fro reflected laser beams are created on the surfaces, which lie on a closed path or a circular path or an ellipse. However, it is also possible for the reflection points 15 to lie on a straight line. The individual partial beams, formed by the reflections, between respectively two opposing reflection points 15 are fanned open toward the mirrors 14a, 14b and are concentrated in a concentration region K, which is situated between the two opposing mirrors 14a, 14b.

The spectrometer 10 also has a housing 16 with openings as gas inlet 17 and gas outlet 18. In the region of the mirrors 14a, 14b, the housing 16 respectively has an opening, which is provided and/or closed off by a window 19a, 19b. Hence, the housing 16 with the windows 19a, 19b forms a closed-off interior 21. During operation, the gas G to be analyzed is routed to the interior 21 through the gas inlet 17 by means of a connected gas supply line and it re-emerges at the opposite end of the housing 16 through the gas outlet 18 arranged there.

During operation, the molecules in the supplied gas flow are ionized on a multiplicity of paths of the laser beam. S and subsequently pass through the potential drop formed by the electrodes 12a, 12b between the ion producing device, formed by the laser 11 and the reflection unit, and the ion collector 13. A potential drop of a few 100 V/cm to over 10,000 V/cm is applied to the electrodes 12a, 12b. The ions produced between the mirrors 14a, 14b are accelerated by the potential drop and impinge on the ion collector 13 at the end of the acceleration distance B.

By way of example, a tunable, miniaturized diode-pumped solid-state laser with a power of a few µJ up to the region above 100 µJ in the UV range serves as laser 11. The individual laser pulses have, for example, a pulse width of less than approximately 5 nanoseconds. The laser has a pulse repetition rate of approximately 1 kHz up to the lower MHz range.

Figure 2:
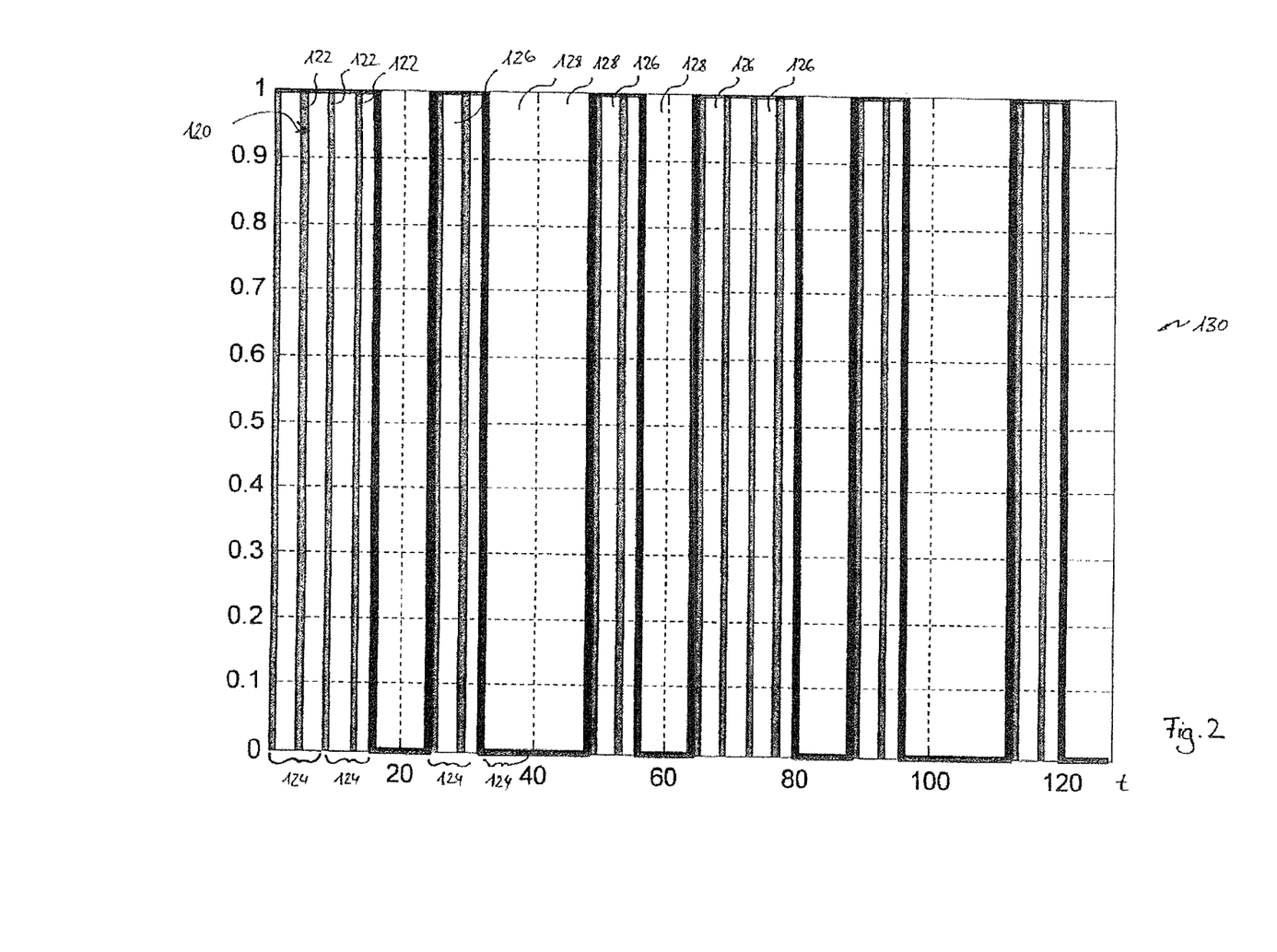
FIG. 2 shows a schematic diagram for illustrating a first exemplary embodiment of a laser pulse sequence modulated by the impression pattern (Hadamard pattern)
Figure 3:
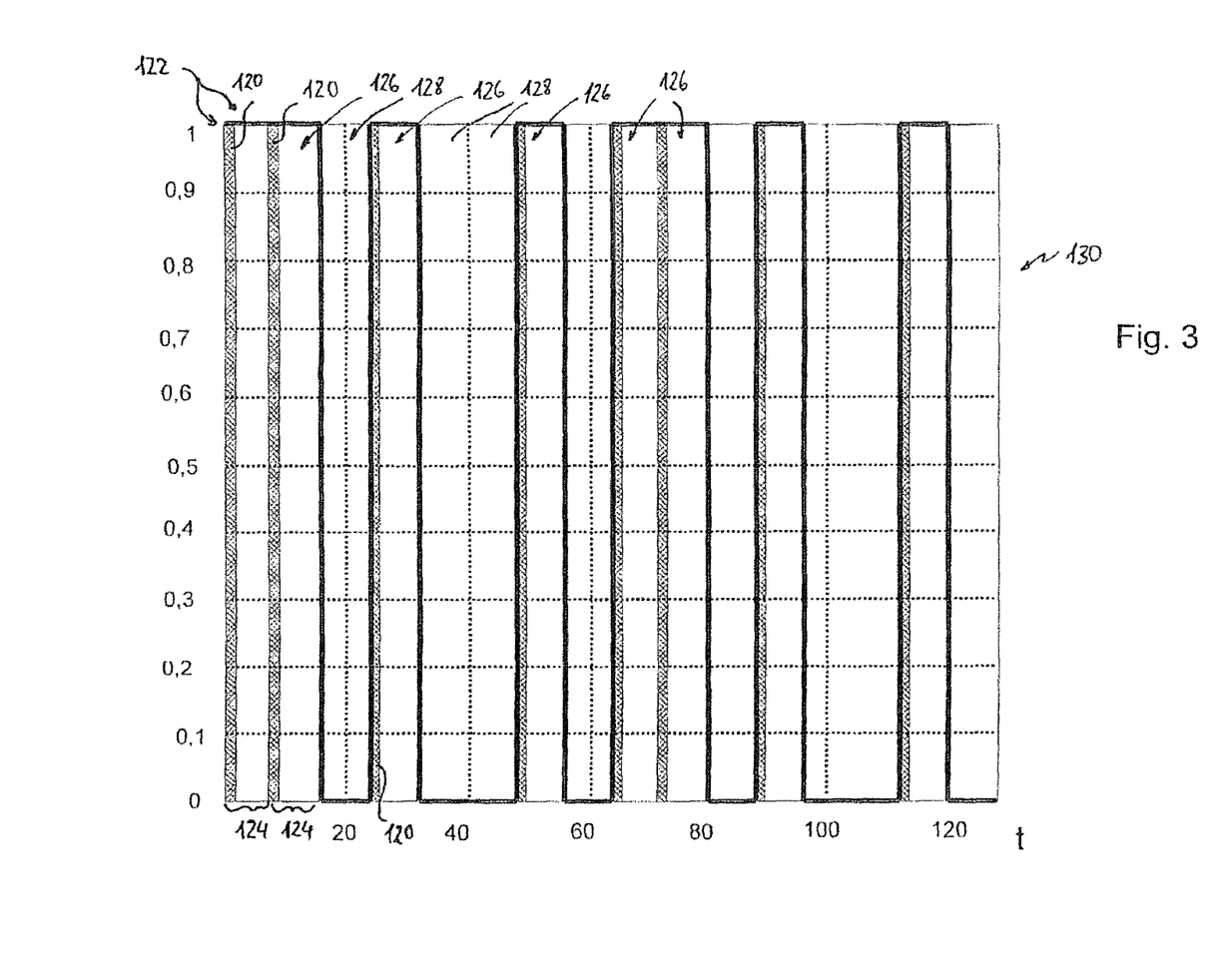
FIG. 3 shows a schematic diagram for illustrating a second exemplary embodiment of a laser pulse sequence modulated by the impression pattern, which constitutes a currently preferred embodiment for a Hadamard-encoded laser pulse sequence.

The laser 11 has a laser device 102 as actual laser beam source, which enables a production of arbitrary laser pulse sequences with direct triggering of individual pulses, and also an encoding or modulating apparatus 104, by means of which a laser pulse sequence 120 (as illustrated in FIG. 2 or FIG. 3) produced by the laser device 102 is encoded or modulated by a predetermined impression pattern.

The detection and/or analysis apparatus 100 is connected to the encoding and/or modulating apparatus 104 and uses the same impression pattern for decoding or demodulating the ion current obtained at the ion collector 13.

As in known LIMS methods and devices, the ions reaching the ion collector 13 are separated by mobility and intensity and produce an ion current at the ion collector 13, which ion current is amplified, digitized and recorded. However, while each recording between two gate electrode openings in known LIMS configurations constitutes a whole drift spectrum, a multiplicity of laser pulses 122 with impressed pattern are used in the configuration and methodology presented here to produce the drift spectrum (as illustrated in e.g., FIG. 2 or 3).

The following text describes a method for measuring the mobility spectra of ions, which are produced by the modulated, rapid-pulsed laser 11. This method can be carried out by means of the laser ionization mobility spectrometry device 106 shown overall in FIG. 1.

The method has a step of modulating the ion current, which originates from a laser-induced two-photon ionization source 108 (with the laser 11 with high repetition rate) and which comprises various ion types with various mobilities. The method furthermore comprises a temporal switching signature with an ion passage of approximately 50%, as a result of which the modulation or signature for the various ion types with respect to one another is shifted in different ways during the time of operation as a result of the different velocities.

The received, quasi-continuous ion-current signal at the end of the drift tube of the laser ionization mobility spectrometry device 106 formed by the housing 16 can be used to uncover, once again, the composition of the ion types according to mobility and intensity by decoding the switching signature (i.e. e.g. the modulation or encoding).

At the same time, it is possible to achieve improved resolution as a result of a second deconvolution step of the diffusion profile.

This method has a cycle with a very long time of operation for the passed substance and for the ions in the ion current.

In the preferred embodiment, rapid time encoding is impressed onto the drift of the ions by using a binary modulation of the ionizing laser pulse frequency, which runs at high constant repetition rates.

Here, the laser 11 acts both as ionization source and as modulating apparatus (or encoding apparatus), and this makes an ion grid or an ion gate at the beginning of the drift chamber dispensable or redundant.

The encoding (modulating, switching) is applied directly on the ion production mechanism—the ionization source 108—and therefore influences each ion type in the same manner. In other words—unlike all previously known ion-gate-based modulated ion mobility spectrometry methods—the encoding does not depend on the electric properties of the ion species.

The encoding is preferably substantially binary and is achieved by modulating the rapid laser pulse sequence in time intervals.

Using laser device 102 enables the production of arbitrary laser pulse sequences with direct triggering of individual pulses. There is no laser emission between the pulses.

The encoding patterns of the various ion types are shifted relative to one another as a result of the different drift velocities during the drift of the ions through the drift tube of the mobility spectrometer 10, and so a complex-looking signal pattern of the ion current is applied at the ion detector.

Instead of the LIMS configuration shown in FIG. 1, it is also possible to provide another LIMS configuration, for example as described in the documents cited at the outset in respect of the LIMS method, accordingly with the encoding and/or modulating apparatus 104 for modulation with corresponding impression patterns.

In the following text, different possible impression patterns for modulating the laser pulse sequence are explained with reference to FIGS. 2 to 7.

Here, FIGS. 2 and 3 show examples of Hadamard encoding. The encoding is substantially binary. There is strictly a switch "on" or "off".

In the example of FIG. 2, the encoding is obtained by modulating a rapid laser pulse sequence with rapidly successive laser pulses 122 in the case of equidistant time intervals 124. Here, an interval 124 can be switched as ON phase (laser pulses 122 are produced) or as OFF phase 128 (laser pulses are not produced; pause). The temporal sequence of the intervals 124 in the form of on phases 126 and off phases 128 are arranged in a characteristic quasi-random pattern.

In the example of FIG. 3, which constitutes the currently preferred embodiment, the Hadamard pattern is impressed onto the laser pulse sequence such that precisely one laser pulse 122 is produced per ON phase 126. In the illustrated example, the laser pulse is produced at the beginning of each ON phase 126. Otherwise the example of FIG. 3 corresponds to that of FIG. 2.

In FIGS. 2 and 3, use is made of a "Hadamard pattern" 130 as impression pattern, as is also already often used in other fields of spectroscopy. However, it is also possible to use other quasi-random patterns.

The Hadamard pattern illustrated in FIGS. 2 and 3 follows the simple Hadamard sequence: 1 1 0 1 0 0 1 0 1 1 . . . .

In the example illustrated in FIG. 2, the interval frequency lies at half the laser pulse frequency. A ratio between laser pulse frequency and interval frequency of up to 5 is feasible (e.g. 50 kHz frequency for encoding and 250 kHz frequency for the laser pulses).

By way of example, in embodiments of the method and the device configured to carry out same, the laser pulse frequency and the interval frequency start at a few kHz and reach up into the MHz range.

Each ON phase (the ones in the Hadamard-simplex-quasi-random-sequence) contains two laser pulses in the example illustrated in FIG. 2 of twice the frequency.

In general, the interval frequency should be less than the sampling frequency. In a prototype, work was undertaken with a 50 kHz sampling frequency, wherein a Hadamard frequency of at most 25 kHz was obtainable. Trials have shown that the Hadamard frequency should ideally be selected to be the same as the laser pulse frequency, which is the same as the interval frequency. Such an example is illustrated in FIG. 3. This makes it simple to carry out the inverse transform in particular. In the example illustrated in FIG. 2 with a number of laser pulses 120 per ON phase, the ion yield is greater but the inverse transform is more complicated in exchange.

Hence, FIG. 3 shows a scheme in which each ON phase 126 only covers one pulse. This is more easily feasible and therefore currently preferred.

In the ion mobility spectrometers, known from the literature mentioned above, with gates at the entry to and exit from the drift distance, e.g., binary codes are utilized such that the opening is left open for 50% of the time. The ions are produced continuously, for example by radioactive radiation. Two gates are required. If these gates are open 50% of the time, they let approximately 50% of all ions through as a statistical average, meaning an increase by a factor of 10 compared to the 1 to 5% in the case of conventional IMS technologies (without encoding the gate times).

In previously known laser IMS, an ion packet is conventionally produced e.g., every 50 ms; then there is a wait until (after 50 ms) the last ions have reached the collector and then another pulse is provided to produce the next ion packet.

However, if a code, e.g. a Hadamard sequence, of 1024 bins is encoded in these 50 ms, then 512-times more ions are produced. Such a method can thus achieve a theoretical improvement by a factor of 512 compared to known LIMS methods.

In the aforementioned practical example, it is currently possible to use e.g., Hadamard frequencies of 0.5 times the sampling frequency, i.e., 25 kHz, for example; that is to say this would be 1250 bins in a 50 ms interval. If 50% thereof are switched as ON phase, this results in 625 times as many ions than in previous methods.

In respect of more details relating to Hadamard encoding, reference is explicitly made to references [4] and [5].

Figure 4A:
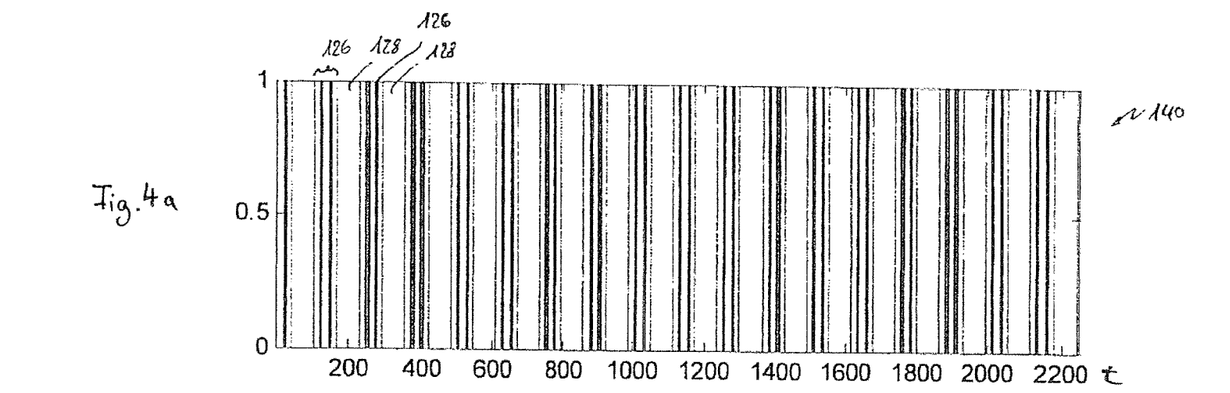
Figure 4B:
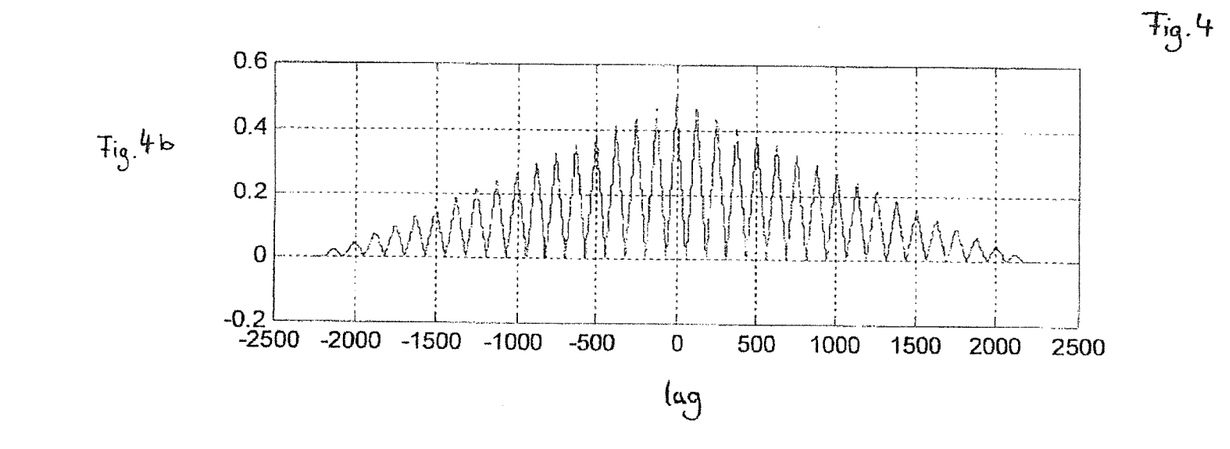
Figure 5:
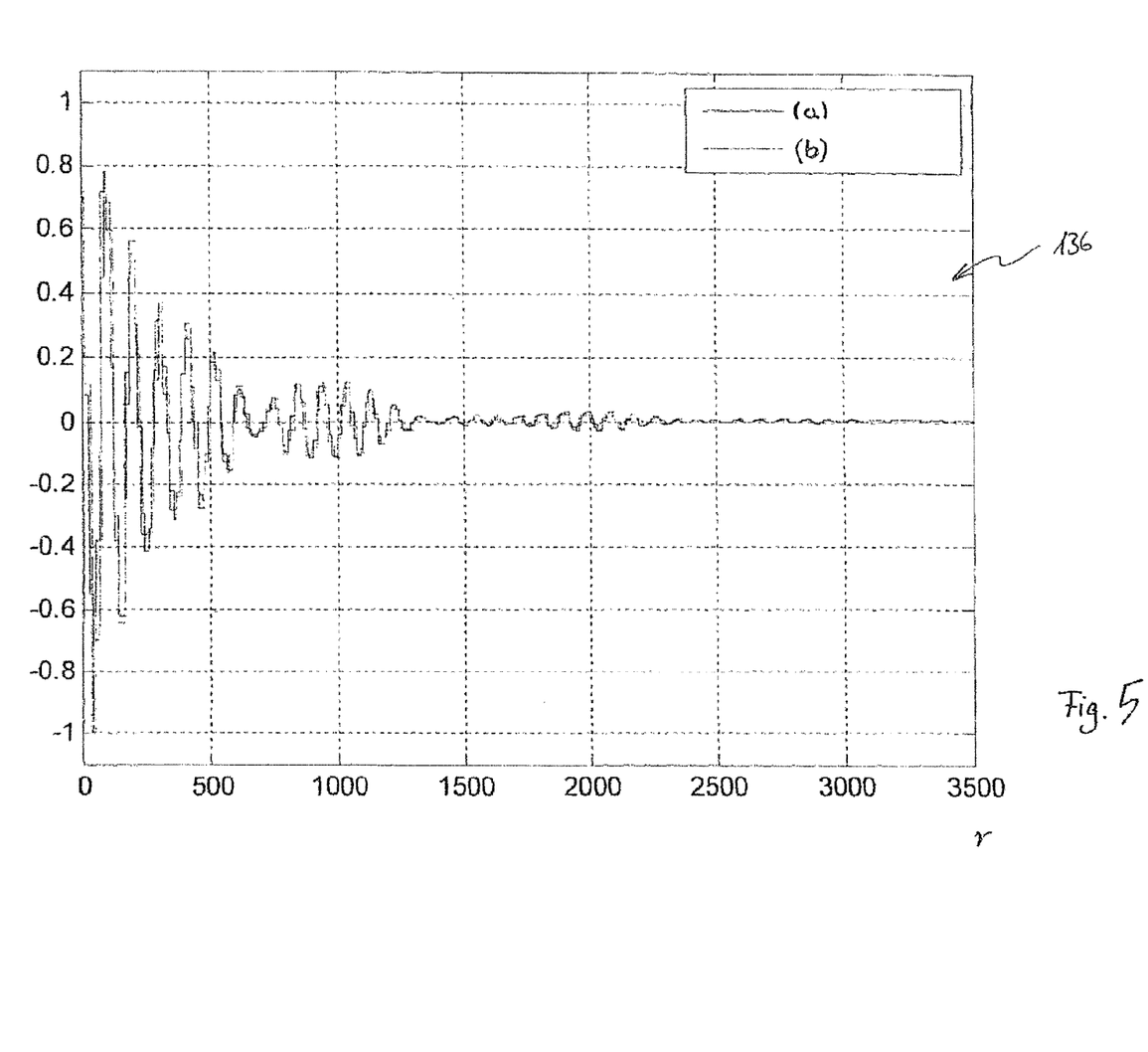
FIG. 5 shows a schematic illustration of an ion interferogram as a result of the FFT encoding indicated in FIGS. 4a and 4b.
Figure 6:
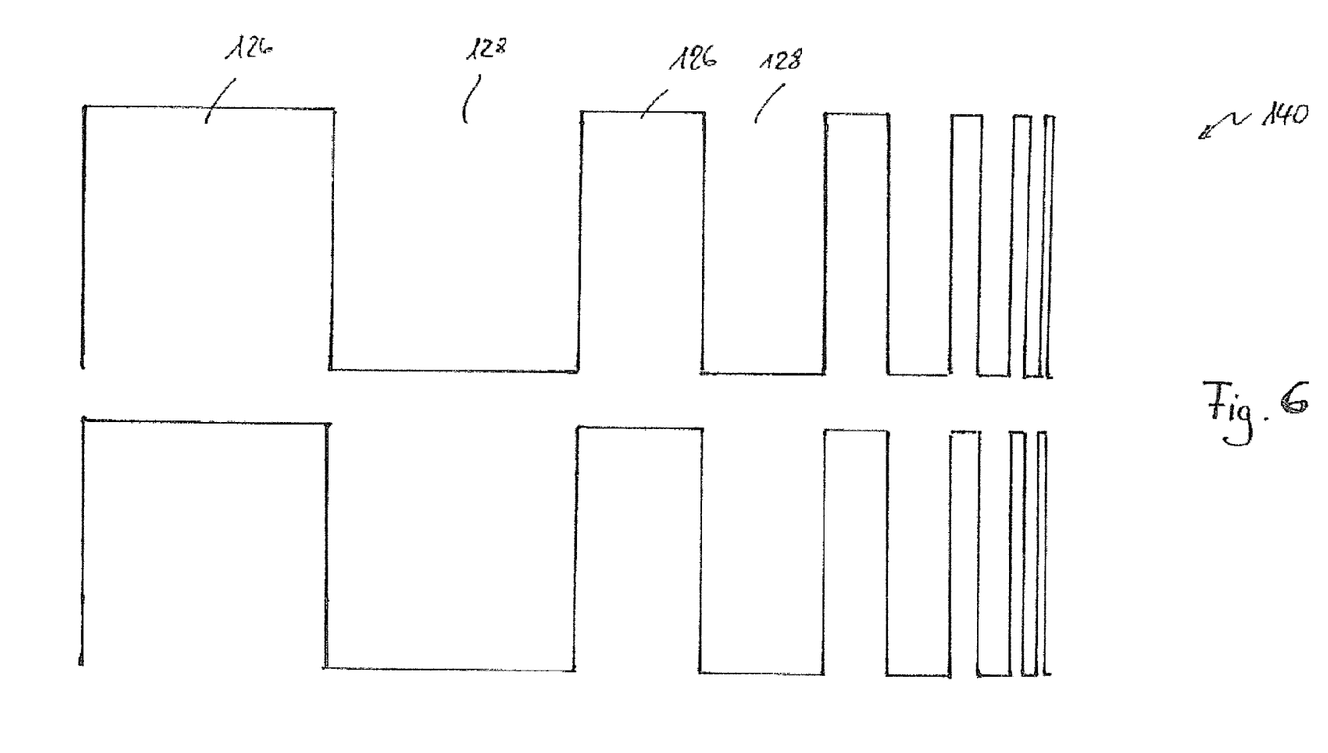
FIG. 6 shows a schematic illustration of a frequency sweep during the FFT encoding.
Figure 7:
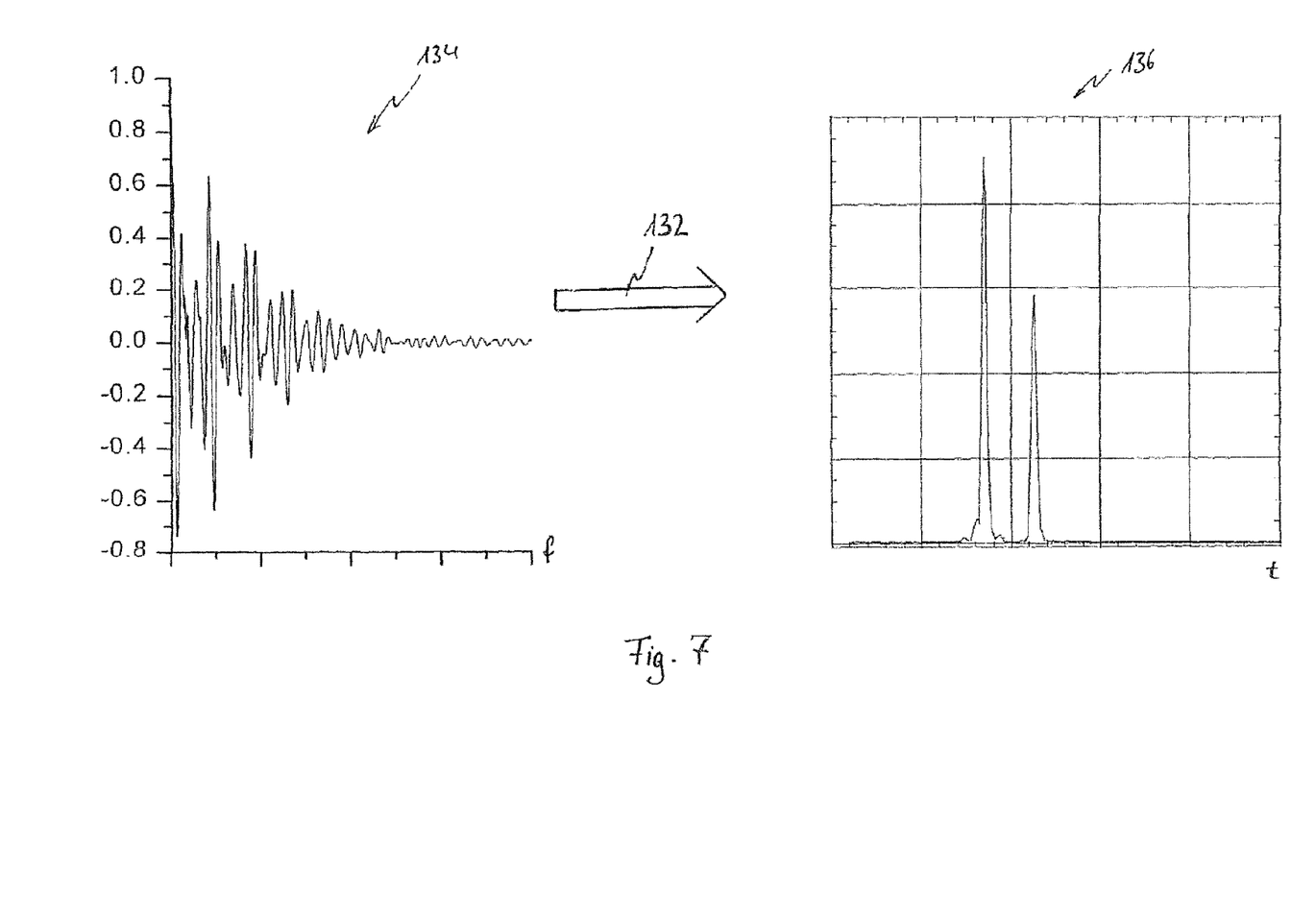
FIG. 7 shows a schematic illustration of a Fourier transform of the ion interferogram for obtaining the spectrum in the time domain.

In the following text, FIG. 4, with subfigures 4a, 4b, and FIGS. 5 to 7 are used to explain an example of FFT encoding in more detail.

Here, the time intervals in respect of the ON phases and OFF phases are equidistant in a periodic sense and correspond to the frequencies of a discrete Fourier transform.

FIG. 4a illustrates the equidistant single-frequency pass function (gate function), with the corresponding autocorrelation, as utilized in the FFT-LIMS mode, being illustrated in FIG. 4a. In the method illustrated here, the pass function is not implemented at gates or ion gates, but by controlling the laser pulses and by electronically controlling the ion collector 13 (ON or OFF).

In one possible embodiment, as indicated schematically in FIG. 6, all required equidistant Fourier transform frequencies are modulated on the ion current during a frequency sweep. The complete set of frequencies leads to a measurement.

FIG. 5 illustrates an example for an interferogram, as is obtained in the FFT-LIMS mode with rectangular waves and the autocorrelation functions thereof, as illustrated in FIGS. 4a and 4b.

A rectangular wave is used as a standard for the impression, as illustrated for example in FIG. 4a. At the same time, the output gate—i.e. the ion collector 13 in the example of FIG. 1—is modulated by the same rectangular wave without a phase shift. What this achieves is that only ions with a drift time of 1/v, 2/vm . . . etc. reach the ion collector 13, in which v denotes the frequency.

From a mathematical point of view, the signal measured at the ion collector 13 can then be represented as an integral (sum) of the autocorrelation function of the rectangular wave multiplied by the drift-time spectrum.

The rectangular wave rw with laser pulses 122 is plotted in FIG. 4a over time t. The autocorrelation function of the rectangular wave is illustrated in FIG. 4b, with the corresponding time lag being specified on the x-axis.

The following then holds true for the signal S for a rectangular wave frequency v:

$$S(v) = \int u(t_d) \times \alpha(t_d) dt_d$$

in which:
$u(t_d)$ is the drift-time spectrum,
$t_d$ is the drift time, and
$\alpha$ is the autocorrelation of the rectangular wave rw with:

$$\alpha = \int (rw(t-t_d) \times rw(t)) dt$$

(a triangular wave as illustrated in FIG. 4b).

An interferogram is obtained after measuring all frequencies, as illustrated at (a) in FIG. 5, which is similar to the DCT (discrete cosine transform) of the drift-time spectrum, likewise illustrated in FIG. 5 at (b). Differences lie in the use of triangular waves rather than sinusoidal waves as a vector-space basis and in other small deviations. The measurements in FIG. 5 are simulated on the basis of discrete frequencies. To this end, a fixed grid of Fourier frequencies is measured for a specific time. Here, the frequency v is plotted on the x-axis and the signal is plotted on the y-axis in FIG. 5. The curve (a) here represents the interferogram, which is referred to as ion interferogram in the following text. The curve (b) represents the discrete cosine transform of the drift-time spectrum. As can be seen, the curves are very similar, which is why it is possible to derive the drift-time spectrum from curve (a) using an inverse discrete cosine transform if a few corrections are carried out.

Another option for measuring different frequencies is illustrated in FIG. 6. FIG. 6 represents a so-called sweep, in which the frequency is tuned. However, the measurement results then differ from the results illustrated in FIG. 5.

As indicated in FIG. 7, the ion mobility spectrum in the time domain 136 can be established by subjecting the ion interferogram 134 to a Fourier transform 132.

Appropriate impression patterns—i.e., for example, the Hadamard pattern or the Fourier transform pattern 140 shown in FIGS. 4a, 4b or 6—is impressed by the encoding and/or modulating apparatus 104 of the laser device 102.

The ion current obtained thereupon is measured by means of the detection and/or analysis apparatus 100 and reproduced, as explained in more detail in the following text.

The physical process and the resultant measured ion current can be described by a mathematical convolution of the encoding pattern with the mobility spectrum for FFT and Hadamard encoding.

A further convolution occurs with the diffusion profile. The diffusion profile can be approximated by a Gaussian curve; it is produced during the drift by diffusion of the ions in the forward and backward direction (spectral deconvolution).

In the example of the Hadamard encoding, the ion current is measured, digitized and stored in its temporal sequence at the ion collector of the drift section. This stored signal pattern can then be decoded by mathematical means, for example:

a) by solving the linear, over-determined set of equations that obtain the mobility spectrum of the ions. This method works with a single set of superposed spectra (multiplex spectra), which is triggered by a pseudo-random code (Hadamard simplex).

b) by measuring a complete set of superposed spectra that are encoded by Hadamard-simplex row vectors, and by re-obtaining the mobility spectrum using the inverse Hadamard matrix.

In the example of FFT encoding, the ion current at the ion collector 13 at the end of the drift section is measured, digitized and stored in its temporal sequence and added for each frequency of the frequency sweep. The example of individual measurements following therefrom constitutes the discrete cosine transform of an individual drift spectrum. The reconstruction can be brought about by deconvolution with the application pattern or by the inverse discrete cosine transform (DCT), from which the drift-time spectrum can then be determined. A few small corrections may additionally be required, as also explained in more detail in citation [1].

The quality of the mathematical transforms (deconvolutions) for decoding is strongly dependent on the noise in the signal. Individual measurements can be summed in order to reduce the noise in the signal. In order to enable the summing up, the encoding pattern should be strictly periodic during a summation procedure, and hence the encoding should not be changed. The length of this period should at least equal the drift time of the slowest ion in the spectrum.

The summed spectrum provides an improved accuracy.

The diffusion spread during the decoding can also be taken into account, and a mobility spectrum with a higher resolution can be obtained by deconvolution with a Gaussian curve.

The two mathematical deconvolutions—the one with the impressed switching pattern and the one with the diffusion curve—can be carried out in a single deconvolution step.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

LIST OF REFERENCE SIGNS

10 Spectrometer
11 Laser
12a Electrode
12b Electrode
13 Ion collector
14a Mirror
14b Mirror
15 Reflection points
16 Housing
17 Gas inlet 18 Gas outlet
19a Window
19b Window
21 Interior
100 Detection and/or analysis apparatus
102 Laser device
104 Encoding and/or modulating apparatus
106 Laser ionization mobility spectrometry device
108 Ionization source
120 Laser pulse sequence
122 Laser pulse
124 Interval
126 ON phase
128 OFF phase
130 Hadamard pattern
134 Fourier transform
136 Time domain
140 Fourier transform pattern
B Acceleration distance
G Gas to be examined
K Concentration region
S Laser beam

The invention claimed is:

1. An ionization method, comprising:
generating a pulse sequence of ionizing radiation that is modulated by a previously known time-variable impression pattern, wherein the pulse sequence of ionizing radiation is modulated in a binary manner, wherein previously known time-variable impression pattern is a quasi-random, pseudo-random, or non-repetitive impression pattern; and
ionizing an analyte to be examined using the generated pulse sequence of ionizing radiation,
wherein the pulse sequence of ionizing radiation has a pulse frequency and is modulated at time intervals by an interval frequency, and
wherein the pulse frequency and interval frequency are greater than 1 kHz and less than 500 MHz.

2. The ionization method as claimed in claim 1, wherein the pulse sequence of ionizing radiation is modulated at equidistant time intervals by the interval frequency, the pulse frequency being an integer multiple of the interval frequency, and each interval constituting either an ON phase during which at least one pulse is produced, or an OFF phase during which no pulses are produced, with the sequence of ON phases and OFF phases being produced according to a Hadamard pattern.

3. The ionization method as claimed in claim 1, wherein the interval frequency has, during the sequence of intervals, ON phases during which at least one pulse is produced, and OFF phases during which no pulses are produced, alternating with one another, with the interval frequency being modified to obtain a frequency spectrum.

4. The ionization method as claimed in claim 1, wherein the ionization is achieved using a pulsed laser, the time sequence of laser pulses of which is modulated by the time-variable impression pattern.

5. The ionization method as claimed in claim 4, wherein the laser is used as ionization source and encoding or modulating apparatus.

6. The ionization method as claimed in claim 4, wherein the pulsed laser device receives the time-variable impression pattern and produces the time sequence of laser pulses.

7. An ion mobility spectrometry method for determining an analyte using ion mobility spectrometry, the method comprising:
generating a pulse sequence of ionizing radiation that is modulated by a previously known time-variable binary impression pattern, wherein the previously known time-variable binary impression pattern is a quasi-random, pseudo-random, or non-repetitive impression pattern;
ionizing an analyte to be examined using the generated pulse sequence of ionizing radiation, wherein the pulse sequence of ionizing radiation has a pulse frequency and is modulated at time intervals by an interval frequency, and wherein the pulse frequency and interval frequency are greater than 1 kHz and less than 500 MHz; and
demodulating, using the impression pattern, an ion current measured after passing over a measuring distance.

8. An ion producing device for an ion mobility spectrometer, comprising:
a pulsed ionization radiation source; and
an encoding or modulating apparatus configured to encode or modulate a pulse sequence from the ionization radiation source with a previously known time-variable impression pattern, wherein the previously known time-variable impression pattern is a quasi-random, pseudo-random, or non-repetitive impression pattern,
wherein the encoding or modulating apparatus is configured to ionize an analyte to be examined using the encoded or modulated pulse sequence of ionizing radiation,
wherein the pulse sequence of ionizing radiation has a pulse frequency and is modulated at time intervals by an interval frequency, and
wherein the pulse frequency and interval frequency are greater than 1 kHz and less than 500 MHz,
wherein the encoding or modulating apparatus is configured to trigger the pulse production in such a manner that the pulse sequence is modulated in a binary manner.

9. The ion producing device as claimed in claim 8, wherein the pulsed ionization radiation source is configured to produce the pulse sequence with the pulse frequency and the encoding or modulating apparatus is configured to switch ON or OFF this production of the pulse sequence.

10. The ion producing device as claimed in claim 9, wherein the encoding or modulating apparatus is configured to switch ON or OFF the pulse sequence at equidistant time intervals with the interval frequency, said interval frequency being less than or equal to the pulse frequency such that the pulse frequency is an integer multiple of the interval frequency, and the encoding or modulating apparatus is configured to produce a sequence of ON phases, during which at least one pulse is produced, and OFF phases, during which no pulses are produced, such that the sequence of ON phases and OFF phases can be produced according to a Hadamard pattern.

11. The ion producing device as claimed in claim 9, wherein the encoding or modulating apparatus is configured to alternately switch the pulse sequence ON and OFF with the interval frequency, which can be modified in order to produce a frequency spectrum.

12. The ion producing device as claimed in claim 8, wherein the pulsed ionization radiation source is a pulsed laser device.

13. The ion producing device as claimed in claim 12, wherein the encoding or modulating apparatus is a software-implemented arrangement for the or in the laser device.

14. An ion mobility spectrometer, comprising:
an ion producing device that includes
a pulsed ionization radiation source; and
an encoding or modulating apparatus configured to encode or modulate a pulse sequence from the ionization radiation source with a previously known time-variable binary impression pattern, wherein the previously known time-variable impression pattern is a quasi-random, pseudo-random, or non-repetitive impression pattern, wherein the encoding or modulating apparatus is configured to ionize an analyte to be examined using the encoded or modulated pulse sequence of ionizing radiation, wherein the pulse sequence of ionizing radiation has a pulse frequency and is modulated at time intervals by an interval frequency, and wherein the pulse frequency and interval frequency are greater than 1 kHz and less than 500 MHz; and a detection or analysis apparatus that includes a demodulator or decoder apparatus configured to demodulate or decode a measured ion current signal using the impression pattern.

\* \* \* \* \*